(12) United States Patent
Tiernan

(10) Patent No.: US 6,692,511 B2
(45) Date of Patent: *Feb. 17, 2004

(54) METHOD OF FORMING A THIN WALLED MEMBER BY EXTRUSION AND MEDICAL DEVICE PRODUCED THEREBY

(75) Inventor: Stephen J. Tiernan, Palo Alto, CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 131 days.

(21) Appl. No.: 09/776,068

(22) Filed: Feb. 2, 2001

(65) Prior Publication Data

US 2001/0004703 A1 Jun. 21, 2001

Related U.S. Application Data

(63) Continuation of application No. 09/301,151, filed on Apr. 28, 1999, now Pat. No. 6,224,803.

(51) Int. Cl.[7] ............................................. G02F 1/1335
(52) U.S. Cl. ..................................................... 606/194
(58) Field of Search ........................ 606/194, 191–193, 606/171, 169, 159; 604/22, 20, 524; 623/1.11

(56) References Cited

U.S. PATENT DOCUMENTS

| 4,330,497 | A |   | 5/1982  | Agdanowski           |         |
|-----------|---|---|---------|----------------------|---------|
| 4,545,390 | A | * | 10/1985 | Leary                | 600/462 |
| 4,842,590 | A | * | 6/1989  | Tanabe et al.        | 604/524 |
| 4,871,506 | A |   | 10/1989 | Moulies et al.       |         |
| 4,884,573 | A |   | 12/1989 | Wijay et al.         |         |
| 4,904,431 | A |   | 2/1990  | O'Maleki             |         |
| 4,906,423 | A |   | 3/1990  | Frisch               |         |
| 4,927,600 | A |   | 5/1990  | Miyashita et al.     |         |
| 4,952,359 | A |   | 8/1990  | Wells                |         |
| 4,998,923 | A |   | 3/1991  | Samson et al.        |         |
| 5,126,089 | A |   | 6/1992  | Johnson et al.       |         |
| 5,135,487 | A | * | 8/1992  | Morrill et al.       | 604/96  |
| 5,143,665 | A |   | 9/1992  | Clubbs et al.        |         |
| 5,156,594 | A | * | 10/1992 | Keith                | 604/96  |
| 5,207,700 | A |   | 5/1993  | Euteneuer            |         |
| 5,207,964 | A |   | 5/1993  | Mauro                |         |
| 5,339,833 | A | * | 8/1994  | Berthiaume et al.    | 600/585 |
| 5,341,818 | A | * | 8/1994  | Abrams et al.        | 600/585 |
| 5,365,943 | A | * | 11/1994 | Jansen               | 600/585 |
| 5,441,055 | A | * | 8/1995  | Ales et al.          | 600/434 |
| 5,480,383 | A | * | 1/1996  | Bagaoisan et al.     | 604/96  |
| 5,499,980 | A |   | 3/1996  | Euteneuer            |         |
| 5,575,965 | A |   | 11/1996 | Caronia et al.       |         |
| 5,603,888 | A |   | 2/1997  | Blizzard et al.      |         |
| 5,609,606 | A | * | 3/1997  | O'Boyle              | 606/194 |

(List continued on next page.)

Primary Examiner—Michael J. Milano
Assistant Examiner—(Jackie) Tan-Uyen T. Ho
(74) Attorney, Agent, or Firm—Fulwider Patton Lee & Utecht, LLP

(57) ABSTRACT

A method of forming a thin-walled polymeric tubular member for an intralumenal device, and the member produced thereby. The thin-walled tubular member extruded using the method of the invention is suitable for use a sleeve for a catheter shaft or balloon. The thin-walled tubular member has a single wall thickness of not greater than about 0.003 inch (0.0076 cm). In the method of the invention, the thin-walled tubular member is formed by co-extruding a thin-walled first polymer layer with a removable second polymer layer, and the two layers are separated by dissolution or physical removal of the second layer, to leave the first layer, with the first polymer layer forming the thin-walled tubular member. Because the method of the invention involves co-extruding a removable second polymer layer along with the thin-walled first polymer layer, conventional tooling dimensions in the extruder may be used.

13 Claims, 4 Drawing Sheets

U.S. PATENT DOCUMENTS

| | | | |
|---|---|---|---|
| 5,843,050 A | * 12/1998 | Jones et al. | 606/194 |
| 6,221,066 B1 | * 4/2001 | Ferrera et al. | 606/1 |
| 6,248,082 B1 | * 6/2001 | Jafari | 600/585 |
| 6,270,521 B1 | * 8/2001 | Fischell et al. | 623/1.11 |
| 6,280,539 B1 | * 8/2001 | Abrams et al. | 600/585 |
| 6,306,124 B1 | * 10/2001 | Jones et al. | 606/194 |
| 6,368,301 B1 | * 4/2002 | Hamilton et al. | 604/103 |

\* cited by examiner

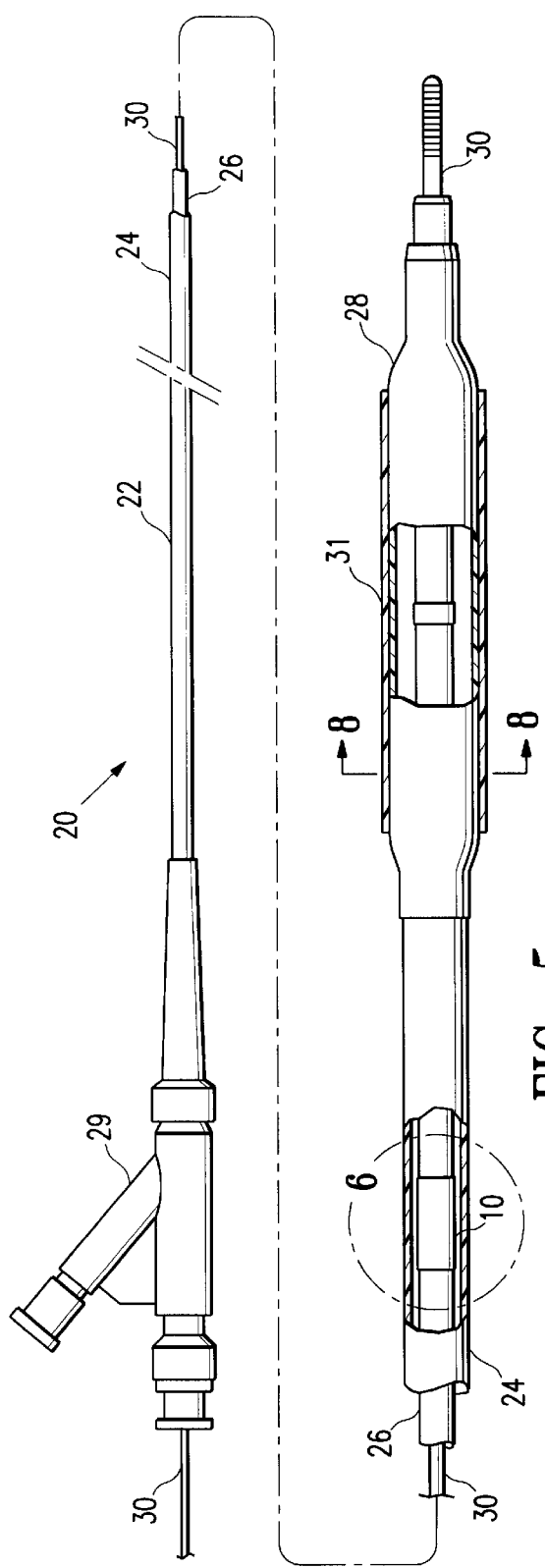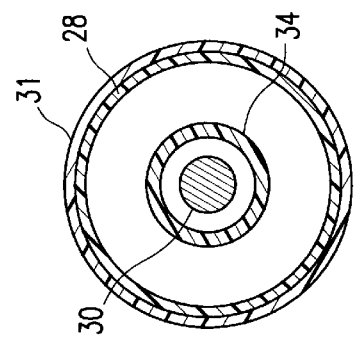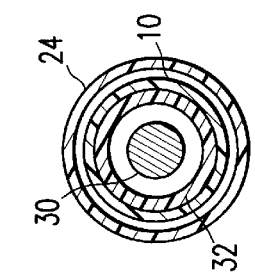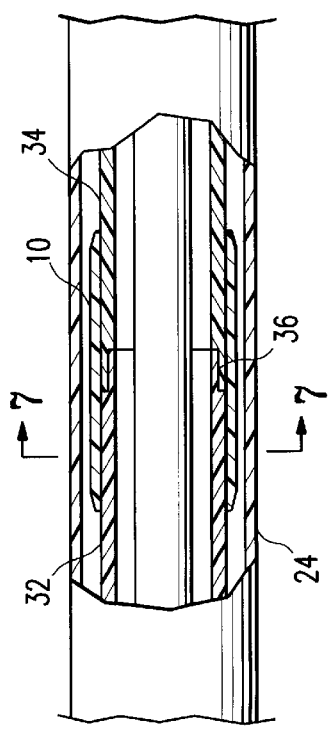

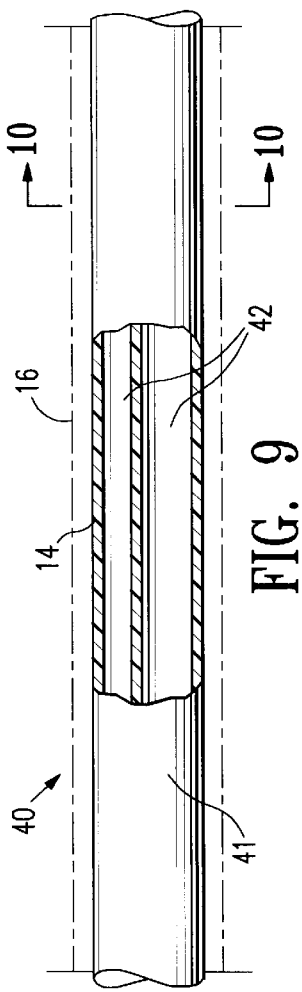
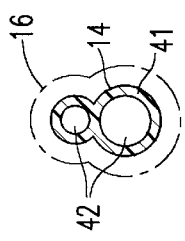
FIG. 9
FIG. 10
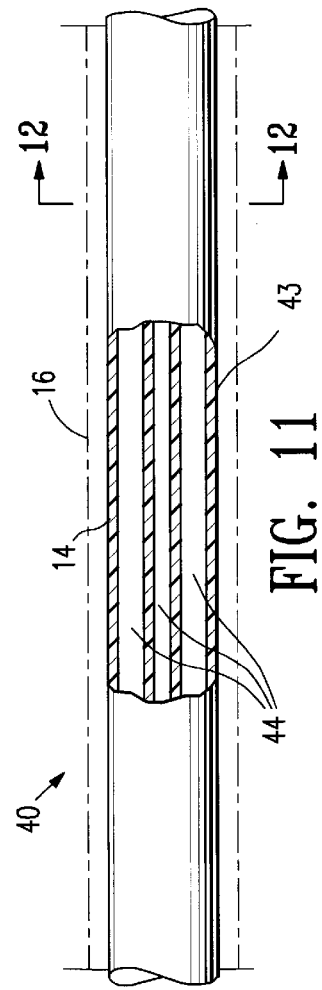
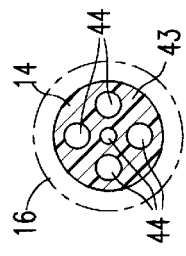
FIG. 11
FIG. 12
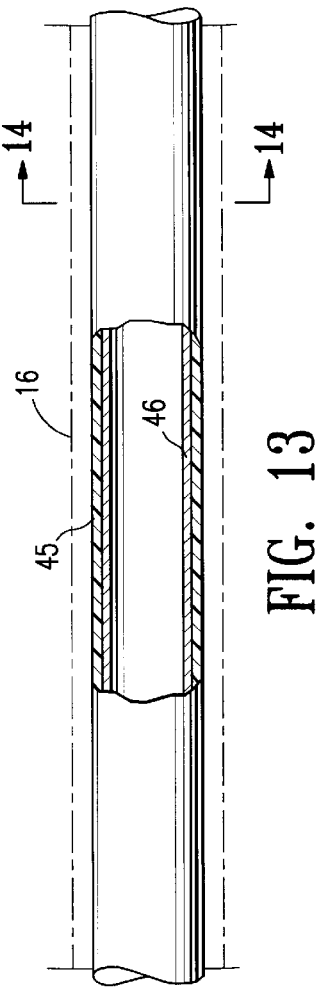
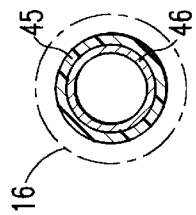
FIG. 13
FIG. 14

METHOD OF FORMING A THIN WALLED MEMBER BY EXTRUSION AND MEDICAL DEVICE PRODUCED THEREBY

This application is a continuation of application Ser. No. 09/301,151 now U.S. Pat. No. 6,224,803, of Steven J. Tiernan, entitled "METHOD OF FORMING A THIN WALLED MEMBER BY EXTURSION AND MEDICAL DEVICE PRODUCED THEREBY," filed on Apr. 28, 1999; which is hereby incorporated herein by reference in its entirety.

BACKGROUND OF THE INVENTION

This invention relates to the field of medical devices, and more particularly to a method of forming a thin-walled member for an intralumenal medical device.

In the design of intralumenal catheters, the progression of improvements has been to decrease the catheter profile, while accommodating the conflicting characteristics of catheter strength and flexibility. These catheter characteristics significantly effect catheter maneuverability and, therefore, the ability to effectively position the catheter at a desired location within a patient. The catheter profile and flexibility are a function of the wall thickness of the various catheter components. While the catheter shaft must have sufficient strength, and therefore sufficient wall thickness, to provide torque transmission and kink resistance, sleeves disposed about the catheter balloon or shaft are generally made very thin. Such sleeves are used to strengthen, protect, or otherwise modify the surface of the catheter balloon or shaft. For example, a sleeve may be provided at the junction of two catheter shaft sections to strengthen the joint. Also, balloon catheters used for stent delivery are typically provided with a protective sleeve between the balloon and the stent mounted thereon. The wall thickness of such tubular sleeves should be very thin to minimize the effects on catheter profile and flexibility.

Polymeric tubular catheter components are typically formed by extrusion, although they may be made by a variety of methods depending on the material used and the desired characteristics of the component. For example, in free extrusion, melted polymeric material passes through an extrusion die over a mandrel. Where a multilayered article is desired, the layers may be co-extruded, or a second layer extruded over an existing polymeric tube. The wall thickness of an extruded tube is a function of the annular gap between the die and the mandrel, and post extrusion processing such as draw-down of the polymeric material. Draw-down is the ratio of the die diameter to the final diameter of the extruded article, and is therefore a measure of the thinning of the extruded article as it exits the extruder.

While extrusion is a preferred technique for forming polymeric tubular catheter components, a thin-walled continuous as-extruded tube has heretofore been unavailable. A variety of technical problems are encountered which prevent the extrusion of a tube having a wall thickness of about 0.003 inch (0.0076 cm) or less, that is suitable for use as a catheter component. For example, such thin-walled tubes loose shape retention during movement through the solidification phase and the take-up system of the extruder. Because of the small annular gap between the die and mandrel used to produce the thin-walled article, the extruded article is prone to melt fracture, i.e. the formation of a rough and irregular surface on the article. Moreover, a tube produced by extrusion using a conventionally sized die and mandrel annular gap cannot be processed into a thin-walled catheter component by drawing-down the tube, because the degree to which wall thickness can be thus reduced is limited. For example, during draw-down to produce a thin-walled tube, the tube wall may tear, or intralumenal air pressure used to maintain the inner diameter dimensions of the tube will produce ballooning of the tube wall.

Therefore, what has been needed is a method of producing a thin-walled tubular catheter component by extrusion. The present invention satisfies these and other needs.

SUMMARY OF THE INVENTION

The invention is directed to a method of forming a thin-walled member for a medical device, and the member produced thereby. The method of the invention generally comprises co-extruding a two layered polymeric member, such as a polymeric tube, and removing and discarding one of the layers, with the remaining layer forming the thin-walled member. The thin-walled member extruded using the method of the invention is suitable for use as a component of an intralumenal catheter.

One aspect of the invention is a thin-walled polymeric member formed by extrusion, and preferably having a single wall thickness of not greater than about 0.003 inch (0.0076 cm). In the method of the invention, the thin-walled member is formed as a thin-walled first polymer layer co-extruded with a removable second polymer layer. The first polymer layer may be co-extruded adjacent either an inner surface or an outer surface of the second polymer layer. The thickness of the thin-walled member of the invention is a function the flow rate of the polymer melt supplied to the co-extrusion die and the draw-down of the extrudate. Controlling the wall thickness of a thin-walled tube is difficult when the tube is extruded as a single layered tube. In contrast, the co-extrusion method of the invention allows the dimensions of the first polymer layer to be sized accurately and controllably. The method of the invention may be used to extrude thin-walled members of a variety of configurations including tubular, oblong, square, and elliptically shaped members, and members having complex shapes such as multilumen members. Additionally, another aspect of the invention is directed to a tubular member, such as a metallic hypotube, having a thin-walled polymer layer extruded thereon. Hypotubes are typically used as a stiff proximal shaft section in a catheter, and details of catheter designs having hypotubes may be found in U.S. Pat. Nos. 4,998,923 and 5,480,383, incorporated by reference herein in their entireties.

Because the method of the invention involves co-extruding a removable second polymer layer along with the thin-walled first polymer layer, a conventional annular gap between the extruder die and mandrel may be used. A conventional annular gap used in extrusion of tubular catheter components is about 0.01 to about 0.015 in (0.025 to about 0.04 cm). Despite the large size of a conventionally sized extruder annular gap, conventional extruder tooling can be used in the method of the invention to produce a thin-walled tubular member having a wall thickness of about 0.003 inch or less because most of the space is filled by the removable second polymer layer.

The removable second polymer layer is typically formed as the outer of the two co-extruded layers in order to facilitate its removal from the thin-walled first polymer layer. However, the removable layer may, alternatively, be on an inner surface of the thin-walled layer. Depending on the nature of the polymers which form the thin-walled and removable layers, the separation of the layers may be by a variety of methods. A presently preferred method involves dissolving the removable layer in a solvent that does not dissolve the thin-walled layer. Alternatively, the removable layer may be physically separated from the thin-walled layer, as by peeling or cutting away of the removable layer.

The method of the invention allows a thin-walled member to be formed by extrusion. The extrudate has excellent shape retention and structural integrity necessary for withstanding the solidification and take-up system of the extruder, due to the removable second polymer layer co-extruded with the thin-walled first polymer layer. The temporarily combined co-extruded layers provide for easy handling and improved kink resistance in the extrudate during post production processing. Moreover, because the method of the invention can be used to extrude a thin-walled tube using a conventionally sized die and mandrel combination, melt fracture in the extrudate is avoided, particularly on the outer surface of the inner layer.

A benefit of the method of the invention is that the thin-walled member can be made extremely thin, i.e. not greater than about 0.003 inch, and with a very accurately maintained thickness along its length. This helps minimize the outer diameter of an intralumenal device having the thin-walled member. Thus, when used for example as a sleeve over the junction of two joined catheter shaft sections or over a balloon, the thin-walled tubular member of the invention provides a low-profiled, smooth sleeve with superior fit over the catheter shaft or balloon.

These and other advantages of the invention will become more apparent from the following detailed description of the invention and the accompanying exemplary drawings.

BRIEF DESCRIPTION OF THE DRAWINGS

FIG. 5 is an elevational view partially in section of a dilatation catheter embodying features of the invention.

FIG. 6 is an enlarged longitudinal cross-sectional view of the catheter shown in FIG. 5 within circle 6.

FIG. 7 is a transverse cross section of the catheter shown in FIG. 5, taken along lines 7—7.

FIG. 8 is a transverse cross section of the catheter shown in FIG. 5, taken along lines 8—8.

FIG. 9 is an elevational view partially in section of a multilumen intralumenal device having two thin-walled tubular members embodying features of the invention.

FIG. 10 is a transverse cross section of the device shown in FIG. 9, taken along lines 10—10.

FIG. 11 is an elevational view partially in section of a multilumen intralumenal device having a thin-walled tubular member with a plurality of lumens.

FIG. 12 is a transverse cross section of the device shown in FIG. 11, taken along lines 12—12.

FIG. 13 is an elevational view partially in section of a multilumen intralumenal device having a thin-walled tubular member on a tubular member.

FIG. 14 is a transverse cross section of the device shown in FIG. 13, taken along lines 14—14.

DETAILED DESCRIPTION OF THE INVENTION

Figure 2:
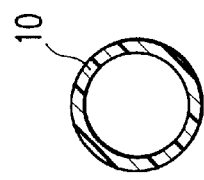
FIG. 2 is a transverse cross section of the device shown in FIG. 1, taken along lines 2—2.
Figure 4:
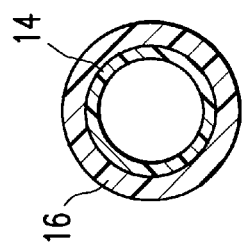
FIG. 4 is a transverse cross section of the tube shown in FIG. 3, taken along lines 4—4.
Figure 1:
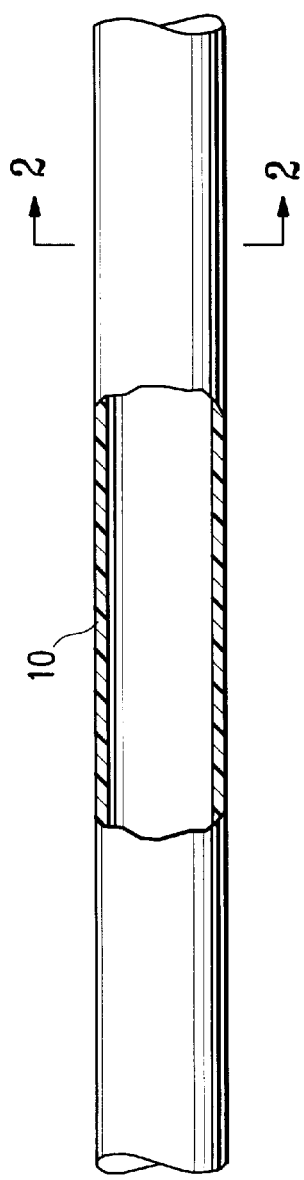
FIG. 1 is an elevational view partially in section of an intralumenal device having a thin-walled tubular member embodying features of the invention.
Figure 3:
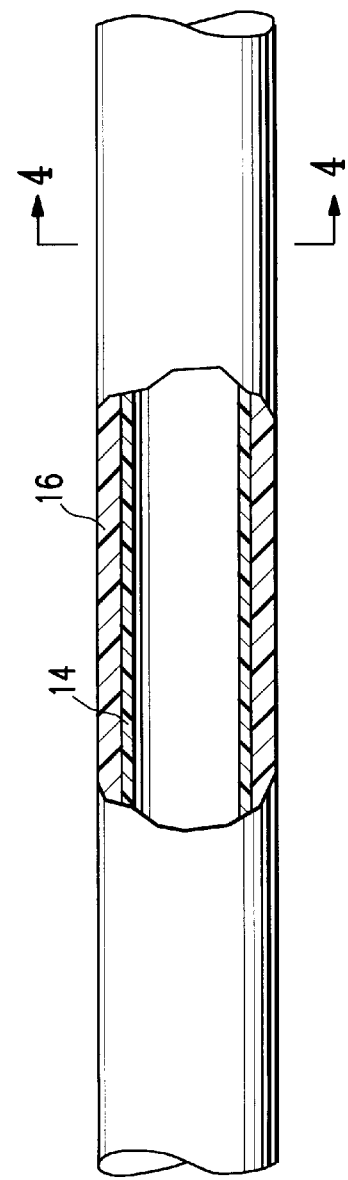
FIG. 3 is an elevational view partially in section of a multilayered extruded tube embodying features of the invention.

FIG. 1 illustrates a thin-walled tubular member 10 of the invention. FIG. 2 illustrates a transverse cross section of the tubular member 10 shown in FIG. 1, taken along lines 2—2. As illustrated in FIG. 3, the thin-walled tubular member 10 for an intralumenal medical device is formed using the method of the invention by co-extruding a first polymer layer 14 with a second polymer layer 16, separating the first polymer layer 14 from the second polymer layer 16, and leaving the first polymer layer 14 to form the thin-walled tubular member 10. Thus, the first polymer layer 14 is the thin-walled tubular member 10 before being separated from the co-extruded second polymer layer 16. FIG. 4 illustrates a transverse cross section of the tubular member 10 shown in FIG. 3, taken along lines 4—4. Although discussed primarily in terms of a thin-walled tubular member, the invention should be understood to include thin-walled members of a variety of shapes.

FIG. 5 illustrates one embodiment of the invention in which the thin-walled tubular member 10 is a sleeve which is disposed about and supports a catheter shaft. The intralumenal device shown in FIG. 5 is a dilatation catheter 20, generally including an elongated catheter shaft 22 with a thin-walled tubular member 10 disposed about the shaft, and an inflatable member 28 on a distal portion and an adapter 29 mounted on the proximal end of a proximal portion. The catheter shaft 22 comprises an outer tubular member 24 and an inner tubular member 26 disposed within the outer tubular member and defining with the outer tubular member annular lumen which is in fluid communication with the inflatable member interior. The inner tubular member has an inner lumen extending therein configured to slidably receive a guidewire 30.

The inner tubular member 26, which is illustrated in more detail in FIG. 6, has a proximal portion 32 and a distal portion 34 secured together at a joint 36 formed by suitable means such as heat or laser fusion or commercially available adhesives. The thin-walled tubular member 10 is disposed about and supports a distal extremity of the proximal portion 32 of the inner tubular member 26 and a proximal extremity of the distal portion 34. FIGS. 7 and 8 illustrate transverse cross sections of the catheter shown in FIG. 5, taken along lines 7—7 and 8—8, respectively. When used as a sleeve about two portions of a catheter shaft, the thin-walled tubular member 10 has a length of about 0.25 inch to about 15 inch (0.5 centimeters to about 40 centimeters), preferably about 0.5 inch to about 2 inch (1.3 centimeters to about 5 centimeters).

The thin-walled tubular member is also well suited for use as a sleeve 31 for the catheter inflatable member 28, as illustrated in FIG. 5. The sleeve 31 may be used as a protective covering for the balloon, to limit expansion of the balloon during inflation, and to decrease the deflation profile of the balloon, and other well known uses for balloon sleeves. When used as a sleeve for a catheter inflatable-member, the thin-walled tubular member 10 has a length of about 0.5 centimeters to about 6 centimeters, preferably about 1.0 centimeters to about 4.0 centimeters. A sleeve for a catheter balloon is sized to extend over at least part of the balloon, typically over the working region of the balloon.

When the inflatable member is used for delivering a stent within a patient, the sleeve should have sufficient length to protect the inflatable member from the stent (not shown) disposed about the inflatable member. The outer diameter (OD) and inner diameter (ID) of the thin-walled tubular member 10 depends on the desired use, but generally, the OD is about 0.038 inch to about 0.058 inch (0.096 to about 0.147 centimeters), and the ID is about 0.035 inch to about 0.055 inch (0.089 to about 0.139 centimeters), for use as a catheter sleeve.

In one aspect of the invention, the thin-walled tubular member 10 is a thin-walled multilumen member 40, such as a tubular multilumen catheter shaft section. In one embodiment, illustrated in FIGS. 9 and 10, the multilumen member 40 comprises a unitary, one piece, extrusion of a plurality of tubular members 41 having lumens 42 therein. In accordance with the invention, the thin-walled multilumen member 40 illustrated in FIG. 9 is formed by co-extruding a first polymer layer 14, typically as an inner layer, with a removable second polymer layer 16. FIGS. 9 and 10 illustrate the thin-walled multilumen member 40 with the removable second polymer layer in phantom. In an alternative embodiment, illustrated in FIGS. 11 and 12, the multilumen member 40 comprises a tubular member 43 having a plurality of lumens 44 therein. In the embodiment illustrated in FIGS. 11 and 12, the thin-walled multilumen member 43 is formed by co-extruding the first polymer layer 14 with a removable second polymer layer 16, shown in phantom, around an outer surface thereof. The second polymer layer 16 may be removed as discussed above, leaving the first polymer layer 14 to form the multilumen member 43. Depending on the number and location of the lumens 44, the wall thickness of the multilumen member 43 may vary across a cross section of the multilumen member. However, in accordance with the invention, at least a section of the multilumen member 43 has a wall thickness of less than about 0.003 inch, as for example the sections between adjacent lumens, or between a lumen and an outer surface of the multilumen member. While the embodiments of the multilumen members 40 illustrated in FIGS. 9 and 11 are illustrated as generally tubular, it should be understood that they may be extruded with a variety of shapes including oblong shapes. When used as a catheter shaft section, the thin-walled tubular member 40 has a length of about 2 to about 150 centimeters.

FIG. 13 illustrates another embodiment of the invention in which the thin-walled member is a layer 45 on a tubular member 46. In one embodiment, tubular member 46 is a metallic hypotube 46, which forms a shaft section, such as a proximal shaft section, of a catheter. The thin-walled member 45 forms a thin coating over an inner or an outer surface of the hypotube 46, which provides, for example, a protective or insulative layer on the hypotube or a bondable surface for joining the hypotube to an adjacent member on the catheter such as a proximal end adapter or a polymeric shaft section. In accordance with the method of the invention, the first polymer layer 14 is co-extruded adjacent an inner surface of the second polymer layer 16, shown in phantom, over the hypotube 46. The second polymer layer 16 may be removed to leave the thin-walled member 45 on the hypotube. FIG. 14 illustrates a transverse cross section of the hypotube 46 and thin-walled member 45 thereon shown in FIG. 13, taken along lines 14—14.

Figure 15:
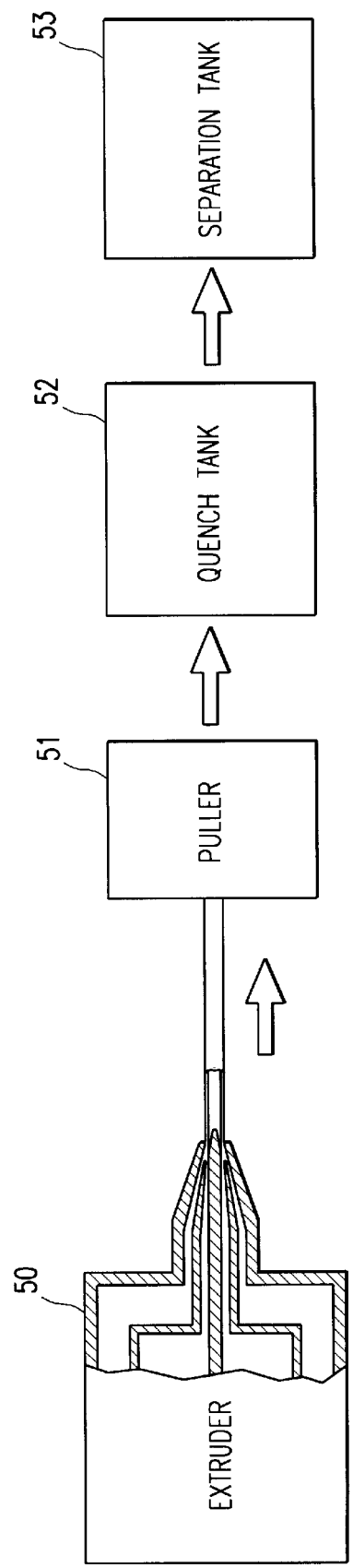
FIG. 15 is a schematic illustration of an apparatus used in the method of the invention.

A presently preferred method of forming the thin-walled tubular member 10 of the invention is by free extrusion using a screw extruder. As illustrated in FIG. 15, the extrudable first polymeric material and the extrudable second polymeric material are added to the extruder 50, and passed through separate heated chambers to melt each polymer. The temperature employed in each chamber is determined by the melting point of polymer passed there through. The melted polymeric materials are then passed through an extrusion die over a mandrel to form a multi-layered elongated tubular extrudate having a first polymer layer and a second polymer layer. The extrusion die and mandrel annular space is conventionally sized, having a gap dimension of about 0.010 inch to about 0.015 inch. In order to produce a thin-walled tubular member 10 having a desired wall thickness, the flow rate of the polymer melt is selected so that the first polymer layer will exit the extruder and then be drawn-down to the desired wall thickness along with the second polymer layer. Because the extrudate is formed by a conventionally sized die and mandrel annular gap, draw down ratios can be selected around normal limits of the first and second polymers which avoid inducing tearing of the molten polymer tube walls. The normal linear draw-down ratio should be about 2.5 to 10, depending on the polymer.

Conventional methods of draw-down may be employed, e.g. the force of gravity or a mechanical puller 51 at the exit of the extrusion die. The tubular extrudate is then cooled, e.g. by submersion in a quench tank 52 located at the exit of the extrusion die. The first and second polymer layers are then separated, as by physically peeling the layers apart or by submersion in a separation tank 53 containing a solvent which dissolves the second polymer layer.

The polymeric materials for the second polymeric layer 16 are chosen to provide ease of separation from the first polymer layer 14 following extrusion. When the method of separation of the two layers is by dissolving the second polymer layer 16, the second polymer layer 16 must be soluble in a suitable solvent in which the first polymer layer 14 is insoluble. A presently preferred material for the second polymer layer is a water soluble polymer, while the material for the first polymer layer is a water insoluble polymer. Suitable water soluble polymers for the second polymer layer 16 include melt-extrudable or shape forming polymers such as polyvinyl alcohol (PVOH) such as VINEX resin, a melt extrudable grade of polyvinyl alcohol available from Texas Polymer Services, Inc, and polyethylene oxide. Alternatively, the second polymer layer 16 may be soluble in a nonaqueous solvent in which the first polymer layer is insoluble 14, as for example, polystyrene soluble in acetone.

Many suitable polymers may be used for the first polymer layer 14, depending on the desired properties of the thin-walled tubular member and the method of separating the two layers. The materials used for the first polymer layer should be chosen for the particular desired properties of the thin-walled tubular member 10, such as lubricity, bondability, and elasticity, and include high density polyethylene (HDPE), and functionalized adhesive resins. The wall-thickness of the thin-walled tubular member will vary depending on the application, although in a preferred embodiment, it is not greater than about 0.003 inch (0.0076 centimeter). It is typically from about 0.0001 to about 0.001 inch (0.00025 to about 0.0025 centimeter) and preferably from about 0.0005 to about 0.002 inch (0.0013 to about 0.005 centimeters) for a sleeve for an angioplasty catheter balloon as illustrated in FIG. 5, or a junction of catheter shaft portions as illustrated in FIG. 6, or other thin walled outer layer on a catheter component. The thin-walled tubular member wall thickness is typically from about 0.0001 to about 0.001 inch (0.00025 to about 0.0025 centimeter) and preferably from about 0.0005 to about 0.002 inch (0.0013 to about 0.005 centimeters) for an outer layer of a catheter shaft as illustrated in FIG. 13. The thin-walled tubular member wall thickness is typically from about 0.0001 to about 0.001 inch (0.00025 to about 0.0025 centimeters), preferably about 0.0005 to about 0.003 inch (0.0013 to about 0.0076 centimeters) for a catheter shaft.

Specific Example first polymer (forming the thin-walled member)=ethylene acrylic acid polymer (PRIMACOR 1410)
second (removable) polymer=PVOH (VINEX)
die gap dimension=0.25 inch
flow rate of polymer exiting the die=0.5 lbs/hour
draw down ratio=3–5

Using these parameters, a tubular member having a first polymer layer and a second polymer layer on an outer surface of the first polymer layer is extruded, for example by coextrusion using screw extruders. The first polymer layer having a wall thickness of about 0.0003 inch and the second polymer layer having a wall thickness of about 0.003 inch. The second polymer layer is removed from the second polymer layer by exposure to a water bath, leaving the thin-walled tubular member having an outer diameter of about 0.024–0.048 inch and an inner diameter of about 0.018–0.036 inch depending on the die and mandrel used, and a wall thickness of about 0.003 inch.

While the present invention has been described in terms of certain preferred embodiments, those skilled in the art will recognize that modifications and improvements may be made to the invention without departing from the scope thereof. For example, a thin-walled tubular member may be used as an outer layer of a shaft to alter the surface characteristics of the shaft without significantly increasing the shaft profile, or as a distal portion of an inner tubular member. Additionally, while the embodiment shown in FIG. 5 is an over-the-wire dilatation catheter 20 having an outer tubular member 24 and an inner tubular member 26, the thin-walled tubular member 12 of the invention may be used in a variety of catheters including rapid exchange catheters, delivery catheters, and guiding catheters.

What is claimed is:

1. An intraluminal device comprising an elongated shaft having a tubular proximal portion, a tubular distal portion, and an extruded polymeric thin-walled tubular member with a wall thickness of about 0.00025 to about 0.0025 cm, the thin-walled tubular member being free of melt fracture and being disposed about and supporting a junction of the proximal and distal portions at which said proximal and distal portions are directly joined to one another.

2. The intraluminal device of claim 1 wherein the elongated tubular shaft is formed at least in part by a metallic tubular member having the thin-walled tubular member disposed on at least a length of the elongated tubular shaft.

3. The intraluminal device of claim 1 wherein the thin-walled tubular member has a wall thickness of about 0.0013 to about 0.0025 centimeters.

4. The intraluminal device of claim 1 wherein the thin-walled tubular member is disposed about and fixes a distal extremity of the shaft proximal portion and a proximal extremity of the shaft distal portion.

5. The intraluminal device of claim 1 wherein thin-walled tubular member has a length of about 1 to about 40 centimeters.

6. The intraluminal device of claim 1 wherein said proximal and distal portions are directly joined to one another by heat fusion.

7. The intraluminal device of claim 1 wherein said proximal and distal portions are directly joined to one another by laser fusion.

8. The intraluminal device of claim 1 wherein said proximal and distal portions are directly joined to one another with the use of an adhesive.

9. The intraluminal device of claim 1 wherein said proximal and distal portions are joined to one another in an interlocking configuration.

10. The intraluminal device of claim 9, wherein said interlocking configuration comprises a lap joint.

11. The intraluminal device of claim 1 wherein the thin-walled tubular member is an outer sleeve extending from a location proximal to the junction to a location distal to the junction, and the wall thickness of the thin-walled tubular member is uniform along its length.

12. An intraluminal device comprising an elongated shaft having a tubular proximal portion, a tubular distal portion, and an extruded polymeric thin-walled tubular member with a wall thickness of about 0.00025 to about 0.0025 centimeters disposed about and supporting a junction of the proximal and distal portions, the wall thickness of the thin-walled tubular member being uniform along its length.

13. An intraluminal device comprising an elongated shaft having a tubular proximal portion, a tubular distal portion, and an extruded polymeric thin-walled tubular member with a wall thickness of about 0.00025 to about 0.0025 cm, the thin-walled tubular member being disposed about and supporting a junction of the proximal and distal portions at which said proximal and distal portions are directly joined to one another, and being formed by a process comprising coextruding the thin-walled tubular member as a first layer of a multilayered coextrudate having a second layer, and separating the thin-walled tubular member from the coextruded second polymer layer to form the thin-walled member having a smooth outer surface.

* * * * *